United States Patent [19]

Grosrey

[11] Patent Number: 5,295,828
[45] Date of Patent: Mar. 22, 1994

[54] APPARATUS FOR FILLING TOOTH ROOT CANALS UNDER VACUUM

[75] Inventor: Jean Grosrey, Arzier, Switzerland

[73] Assignee: Meditec S.A., Ecublens, Switzerland

[21] Appl. No.: 955,533

[22] Filed: Oct. 1, 1992

[30] Foreign Application Priority Data

Oct. 18, 1991 [CH] Switzerland ............ 03065/91

[51] Int. Cl.⁵ .............................................. A61G 5/02
[52] U.S. Cl. ....................................... 433/81; 433/224
[58] Field of Search ................................. 433/81, 224

[56] References Cited

U.S. PATENT DOCUMENTS

| | | |
|---|---|---|
| 4,021,921 | 5/1977 | Detaille ............... 433/80 |
| 4,993,947 | 2/1991 | Grosrey ............... 433/81 |

FOREIGN PATENT DOCUMENTS 1412766  7/1988  U.S.S.R. .................... 433/224

OTHER PUBLICATIONS

Prof. Dr. med. Dr. med. dent. Gustav Korkhaus and Dr. med. dent. Rudolf Alfter: "Die Vakuumwurzelbehandlung" (Vacuum Treatment of Roots), Forschungsberichte des Wirtschafts-und Verkehrsministeriums Nordrhein-Westfalen; Westdeutscher Verlag, Cologne and Opladen, 1958 and translation of pp. 25-29 which related to the description of the apparatus.

Primary Examiner—John J. Wilson
Attorney, Agent, or Firm—Pennie & Edmonds

[57] ABSTRACT

The apparatus comprises a filling nozzle having a conical part so that it can fit in a leaktight manner on to a burred aperture in a tooth to be filled. The nozzle has a suction tube and a first annular channel connected to the suction tube and coming out into the dental cavity in order to create a vacuum therein. A second central channel serves to bring a filling paste from a reservoir to the dental cavity. The cross-section of flow of the first channel is several times smaller than that of the second channel, so that the paste travels much more slowly in the first channel than in the second, under the effect of the partial vacuum in the dental cavity.

9 Claims, 1 Drawing Sheet

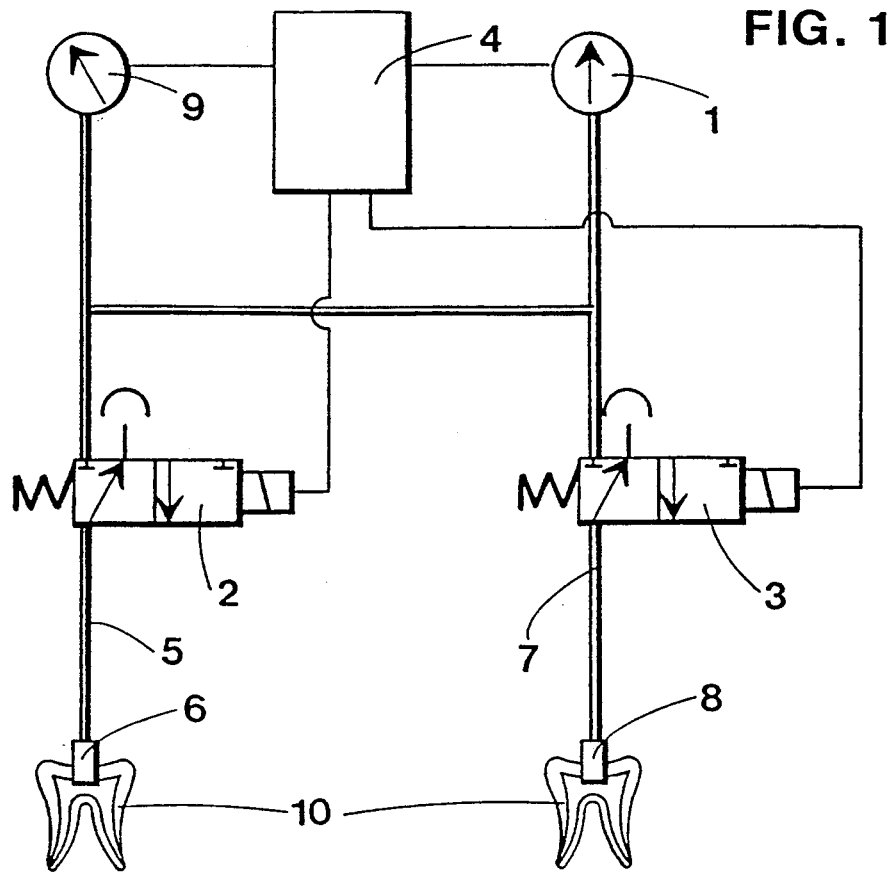
FIG. 1
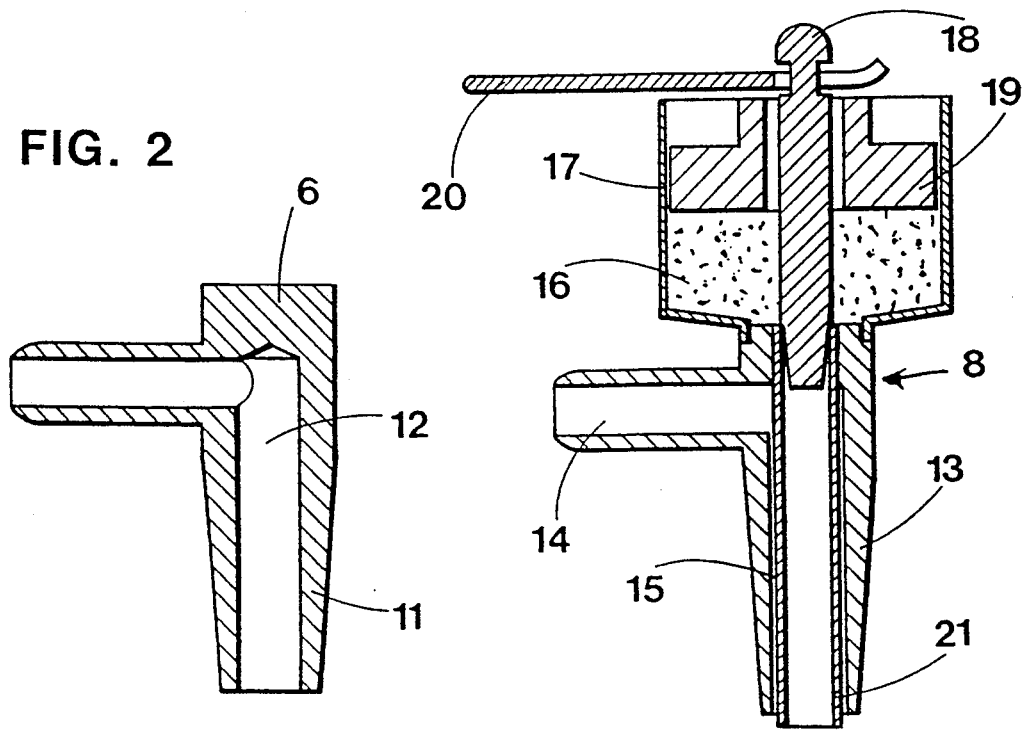
FIG. 2
FIG. 3

APPARATUS FOR FILLING TOOTH ROOT CANALS UNDER VACUUM

BACKGROUND OF THE INVENTION

Tooth canals are currently filled by the "lentula" method or by using gutta-percha cones. These two methods are satisfactory but fill the lateral canals randomly and in any case do not fill the canaliculi. Processes involving the injection of hot gutta-percha appeared a few years ago on the American market, but the results do not yet seem to be convincing. The process is very difficult to apply in the case of canals treated by the hydraulic method, as described in U.S. Pat. No. 4,993,947.

The latter patent describes a vacuum filling process which has shown a few shortcomings. The friction of the plunger of the syringe has to be compensated by a slight pressure on said plunger, which runs the risk of causing overflowing at the apex. Filling paste often passes into the suction tube connecting the nozzle to the vacuum pump.

The vacuum filling of devitalized teeth was proposed as long ago as 1958 (Prof. Dr.med.Dr.med.dent. Gustav Korkhaus and Dr.med.dent. Rudolf Alfter: Die Vakuumwurzelbehandlung (Vacuum Treatment of Roots), Forschungsberichte des Wirtschaft- and Verkehrsministeriums Nordrhein-Westfalen; Westdeutscher Verlag, Cologne and Opladen, 1958). However, the equipment used at the time was cumbersome and rather inefficient and was poorly suited to dental technique. The three-way valve was not easy to use and the dead volumes were very large.

SUMMARY OF THE INVENTION

The aim of the present invention is to provide a device for filling root canals under vacuum which is effective and devoid of the disadvantages of the devices known in the prior art. The present invention relates to an apparatus for filling tooth root canals under vacuum, comprising a filling nozzle designed to fit in a leaktight and detachable manner into a burred aperture of a tooth, and abutting on the dental cavity in the tooth to be filled, and, in this nozzle: a suction tube for connection to a source of partial vacuum, a reservoir of filling paste, a first channel which is connected on the one hand to the inside of the dental cavity when the nozzle is fitted on to a tooth, and on the other hand to said suction tube, so as to produce a vacuum in the dental cavity, and a second channel, one end of which abuts on the dental cavity and the other end of which is connected to said reservoir of filling material, via a means for controlling the communication between this reservoir and this second channel, in order to control the filling of the dental cavity with the filling material coming from this reservoir, under the action of the partial vacuum in the dental cavity, said apparatus being characterized in that the cross-section of flow of said first channel is several times smaller than that of said second channel, so that, when the level of the filling material in the dental cavity reaches the lower end of this first channel, said filling material is then sucked into this first channel and travels much more slowly inside it than in the second channel, under the effect of the partial vacuum in the dental cavity, but is sufficiently large to enable the necessary vacuum to be created in an acceptable time, so as to ensure that this cavity is correctly filled with this material.

BRIEF DESCRIPTION OF THE DRAWINGS

The attached drawings show, by way of example, an embodiment of the apparatus forming the subject of the invention.

FIG. 1 is a general diagram of an embodiment of the apparatus according to the invention.

FIG. 2 is a diagrammatic cutaway view of a nozzle for drying root canals, belonging to this embodiment according to FIG. 1.

FIG. 3 is a cutaway view analogous to FIG. 2 but showing, in section, a filling nozzle also belonging to this embodiment of the apparatus.

DETAILED DESCRIPTION OF THE INVENTION

The general diagram (FIG. 1) shows a four-stage diaphragm vacuum pump 1, a three-way solenoid valve 2 for drying, a three-way solenoid valve 3 for filling, and an electronic means 4 for controlling the assembly. The whole is housed in a casing not shown in the diagram. The solenoid valve 2 for drying is joined by a tube 5 to a drying nozzle 6, and the solenoid valve 3 for filling is joined by a tube 7 to a filling nozzle 8.

A pressure-sensitive switch 9 makes it possible to monitor the quality of the vacuum, enabling any leaks to be detected, in particular in the taper joint between the nozzle and the treated tooth.

By means of the electronic control 4, the practitioner can choose to direct the vacuum either through the drying nozzle 6 in order to dry the tooth after the canal has been cleaned, or through the nozzle 8 for filling after drying. A rest position is also provided. This control 4 also comprises an alarm (not shown) which is triggered by the pressure-sensitive switch if the latter has detected an insufficient vacuum.

The drying nozzle 6 (FIG. 2) is no more than a joint between the vacuum supply tube 5 and the tooth to be treated, 10. This joint is characterized by a cone 11 with a conicity of 4° so that it ensures leak-tightness and can easily be fitted into the burred aperture of the tooth, produced with a shaped bur, on the occlusal face of the tooth. Furthermore, the vacuum supply tube 12 is sufficiently large not to cause too great a pressure drop.

In fact, during the drying phase, the water contained in the treated canal or canals is vaporized by suction and a substantial flow of vapour will pass through the nozzle.

The filling nozzle 8, which is shown in section in FIG. 3, comprises a cone 13 identical to the cone 11 of the drying nozzle 6. The vacuum is created in the tooth by means of a suction tube 14 and an annular channel 15. The filling paste 16 has been introduced into a reservoir 17 after a closing pin 18 has been placed in position. A small free plunger 19 is placed on the filling paste so that the reservoir empties homogeneously when the paste is sucked out by the vacuum.

To fill the treated canal or canals, the practitioner gently presses a small control lever 20, which raises the closing pin 18 and thereby opens that end of a tube 21 which is adjacent to the reservoir 17, thus enabling the paste to be sucked into the tooth through said tube. The paste will now penetrate all the interstices in the root system, and even the canaliculi if these have been cleaned by cavitation (which is the case when the treatment has been carried out by the process described in U.S. Pat. No. 4,993,947).

It is obvious that the paste will also be sucked into the channel 15 leading to the suction tube 14 connected to the vacuum pump. To avoid this disadvantage, this passage is given very precise dimensions. In fact, if the passage is too narrow, the pressure drop caused by the flow of the paste is very large and the paste will take several minutes to reach the suction tube 14. Conversely, as regards the necessary quality of vacuum (about 10 hPa), the pressure drop created by the passage of the air molecules enclosed in the volume of the root system is again very large. The volume of gas to be removed is small (less than half a cubic centimetre) because the system has been dried beforehand. Experience has shown that a cross-section of 0.5 mm² for a length of 9 mm is an acceptable compromise. The vacuum of 10 hPa is reached after one minute in the case of a normal root system. Paste having a fluidity conventionally used in dentistry will take one minute to reach the tube 14, which is more than sufficient to switch the solenoid valve 3 for filling. The concentric construction of 13 and 21 was chosen as being the most suitable. It is self-evident that, in a variant, the annular tube 15 can be replaced with a small tube placed next to the paste supply tube 21.

Provision is advantageously made for at least the conical part 13 of the nozzle to be transparent, so that the dentist can observe the slow rise of the paste in the channel 15 and know the right moment to stop the paste leaving the reservoir 17 and entering the dental cavity.

As indicated above, the vacuum pump 1 is preferably a four-stage diaphragm pump capable of creating a vacuum of 10 hPa. In view of the small volumes involved, the output can be very low. The dimensions of such pumps are nowadays very acceptable: 700 cc for a weight of one kilogram.

A small heater of 1 to 2 watts (not shown in FIG. 3) can surround the reservoir 17 so that the fluidity of the filling product used can be modified at will. This small heater is very convenient, in particular for filling the canals with gutta-percha intended for this purpose.

I claim:

1. In an apparatus for filling tooth root canals under vacuum, comprising a filling nozzle (8) designed to fit in a leaktight and detachable manner into a burred aperture of a tooth, and abutting on the dental cavity in the tooth to be filled, said nozzle including a suction tube (14) for connection to a source of partial vacuum, a reservoir (17) of filling paste, a first channel (15) which is connected at one end to the inside of the dental cavity when the nozzle is fitted on to a tooth and at another end to said suction tube (14) so as to produce a vacuum in the dental cavity; a second channel (21), one end of which abuts on the dental cavity and another end of which is connected to said reservoir (17) of filling material; and means (18) for controlling the communication between the reservoir (17) and the second channel (21) in order to control the filling of the dental cavity with the filling material coming from the reservoir under the action of the partial vacuum in the dental cavity; the improvement wherein: the cross-section of flow area of said first channel (15) is of the order of ten times smaller than that of said second channel (21), so that, when the level of the filling material in the dental cavity reaches the lower end of said first channel (15), said filling material is then sucked into said first channel and travels, under the effect of the partial vaccum in the dental cavity, much more slowly inside said first channel (15) than in the second channel (21) but is sufficiently large to enable the necessary vacuum to be created so as to ensure that this cavity is correctly filled with this material.

2. An apparatus according to claim 1, characterized in that the second channel (21) is cylindrical and coaxial with the nozzle (13), said nozzle being conical and the first channel (15), is of annular cross-section, concentrically surrounding the second channel (21).

3. An apparatus according to claim 1, characterized in that the cross-section of flow of the above-mentioned first channel (15) is of the order of 0.5 mm² for a length of this channel of approximately 9 mm.

4. In an apparatus for filling tooth root canals under vacuum, comprising a filling nozzle (8) designed to fit in a leaktight and detachable manner into a burred aperture of a tooth, and abutting on the dental cavity in the tooth to be filled, said nozzle including a suction tube (14) for connection to a source of partial vacuum, a reservoir (17) of filling paste, a first channel (15) which is connected at one end to the inside of the dental cavity when the nozzle is fitted on to a tooth and at another end to said suction tube (14) so as to produce a vacuum in the dental cavity; a second channel (21), one end of which abuts on the dental cavity and another end of which is connected to said reservoir (17) of filling material; and means (18) for controlling the communication between the reservoir (17) and the second channel (21) in order to control the filling of the dental cavity with the filling material coming from the reservoir under the action of the partial vacuum in the dental cavity; the improvement wherein: the nozzle is conical; the first channel is annular in cross-section and concentrically surrounds the second channel; the second channel is coaxial with the nozzle; and the cross-section of flow area of said first channel (15) is several times smaller than that of said second channel (21), so that, when the level of the filling material in the dental cavity reaches the lower end of said first channel (15), said filling material is then sucked into said first channel and travels, under the effect of the partial vacuum in the dental cavity, much more slowly inside said first channel (15) than in the second channel (21) but is sufficiently large to enable the necessary vacuum to be created so as to ensure that this cavity is correctly filled with this material.

5. An apparatus according to any one of claims 1, 4, 2 and 3, characterized in that the wall of the first channel (15) is transparent, over at least part of its length, from that end which will be in the dental cavity when the nozzle is fitted on to a tooth, so that the operator can see the progression of the filling material in this first channel (15) and thus know when it is necessary to stop the material leaving said reservoir (17).

6. In an apparatus for filling tooth root canals under vacuum, comprising a filling nozzle (8) designed to fit in a leaktight and detachable manner into a burred aperture of a tooth, and abutting on the dental cavity in the tooth to be filled, said nozzle including a suction tube (14) for connection to a source of partial vacuum, a reservoir (17) of filling paste, a first channel (15) which is connected at one end to the inside of the dental cavity when the nozzle is fitted on to a tooth and at another end to said suction tube (14) so as to produce a vacuum in the dental cavity; a second channel (21), one end of which abuts on the dental cavity and another end of which is connected to said reservoir (17) of filling material; and means (18) for controlling the communication between the reservoir (17) and the second channel (21) in order to control the filling of the dental cavity with the filling material coming from the reservoir under the action of the partial vacuum in the dental cavity; the improvement wherein: the cross-section of flow area of said first channel (15) is several times smaller than that of said second channel (21), so that, when the level of the filling material in the dental cavity reaches the lower end of said first channel (15), said filling material is then sucked into said first channel and travels, under the effect of the partial vacuum in the dental cavity, much more slowly inside said first channel (15) than in the second channel (21) but is sufficiently large to enable the necessary vacuum to be created so as to ensure that this cavity is correctly filled with this material; and the wall of the first channel (15) is transparent, over at least part of its length, from that end which will be in the dental cavity when the nozzle is fitted on to a tooth, so that the operator can see the progression of the filling material in the first channel (15) and thus know when it is necessary to stop the material leaving said reservoir (17).

7. An apparatus according to any one of claims 1, 4 and 6, characterized in that the reservoir (17) of filling material is located at the end of the second channel (21) opposite the end which will fit into the dental cavity, said control means is a manual control device (18, 20) for controlling the communication between this reservoir (17) and the end of second channel (21) which is opposite the end which will fit into the dental cavity.

8. An apparatus according to claim 7, characterized in that said control device has a free plunger (19) located in said reservoir (17), which is cylindrical, said plunger resting on the free surface of the filling material (16) present in this reservoir and remaining in contact with this surface while this material is sucked into the dental cavity.

9. An apparatus according to any one of claims 1, 4 and 6, characterized in that a small heater of one to two watts surrounds the reservoir 17 so that the fluidity of the filling material, such as paste or gutta-percha, can be modified at will.

* * * * *